United States Patent [19]

Hanauer et al.

[11] 4,030,690

[45] June 21, 1977

[54] MEDICAL EQUIPMENT DEVICE FOR CONTROLLING DISPOSITIONS OF INTRAVENOUS BOTTLES

[75] Inventors: Burton C. Hanauer, Avon; Charles Richard Patton, Bloomington, both of Minn.

[73] Assignee: Hanauer Machine Works Incorporated, Avon, Minn.

[22] Filed: Dec. 29, 1975

[21] Appl. No.: 644,833

Related U.S. Application Data

[63] Continuation-in-part of Ser. No. 515,438, Oct. 16, 1974, abandoned.

[52] U.S. Cl. .............................. 248/311.3; 248/125; 248/104; 248/204
[51] Int. Cl.[2] ........................................ A47K 1/08
[58] Field of Search ...................... 24/314, DIG. 18; 211/74, 75; 248/122, 124, 125, 204, 229, 309–316, 318, 102–107

[56] References Cited

UNITED STATES PATENTS

| 1,179,286 | 4/1916 | Crimmel | 248/315 X |
|---|---|---|---|
| 1,474,593 | 11/1923 | Jennings | 248/105 |
| 1,624,830 | 4/1927 | Emsley | 248/311 X |
| 1,729,531 | 9/1929 | Wolever | 248/105 |
| 2,050,622 | 8/1936 | Menk | 248/105 |
| 2,056,096 | 9/1936 | Etter | 248/311 X |
| 2,180,042 | 11/1939 | Ettinger | 211/74 UX |
| 2,349,054 | 5/1944 | Phipps | 248/106 |
| 2,893,672 | 7/1959 | Vardan | 248/102 |
| 3,313,511 | 4/1967 | Koerner et al. | 248/505 X |
| 3,519,231 | 7/1970 | Miller | 248/106 |

*Primary Examiner*—Lawrence J. Staab
*Attorney, Agent, or Firm*—Orrin M. Haugen

[57] ABSTRACT

An intravenous bottle retaining means which comprises a support bracket adapted to be retained on an intravenous bottle post or standard, with the bracket having a bottle receiving means at the outer end thereof. The bottle receiving means is in the form of an open ended generally radially flexible rubber split sleeve with projection means adjacent the bottom end thereof for releasably supporting an intravenous bottle within the split sleeve. Means are also provided for releasably drawing the opposed free edges of the split sleeve arcuately toward each other for additional bottle support.

3 Claims, 4 Drawing Figures

U.S. Patent  June 21, 1977  4,030,690
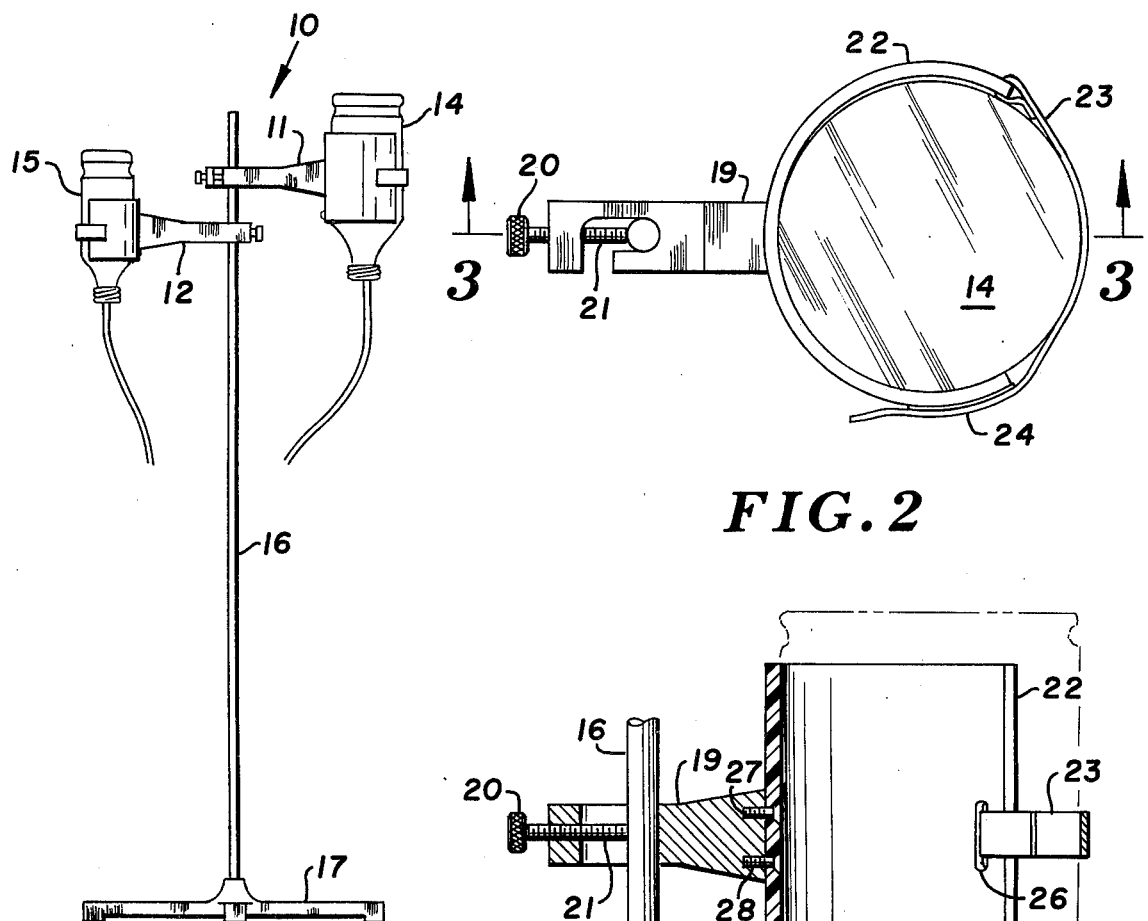
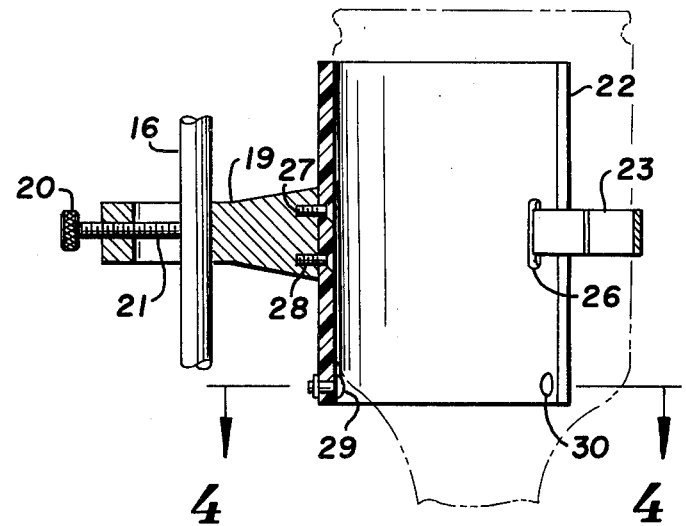
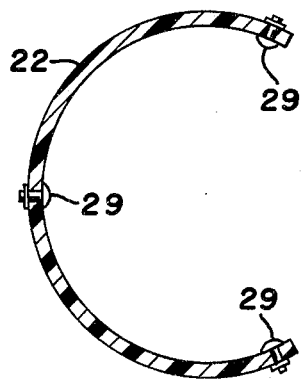
FIG.1
FIG.2
FIG.3
FIG.4

MEDICAL EQUIPMENT DEVICE FOR CONTROLLING DISPOSITIONS OF INTRAVENOUS BOTTLES

CROSS-REFERENCE TO RELATED APPLICATION

The present application is a Continuation-in-Part of our co-pending application Ser. No. 515,438, filed Oct. 16, 1974 now abandoned and entitled "MEDICAL EQUIPMENT DEVICE FOR CONTROLLING DISPOSITIONS OF INTRAVENOUS BOTTLES," and assigned to the same assignee as the present application.

BACKGROUND OF THE INVENTION

The present invention relates generally to an intravenous bottle retaining means, and more specifically to such a bottle retaining means which is particularly adapted for firm releasable retention of intravenous bottles in operative disposition.

Intravenous bottles containing fluids are in wide use in the medical field. Intravenous bottles are utilized to retain fluids for metered dispensing into the patient's system, with these devices normally being employed for a patient during rest or repose. Frequently, varying quantities of fluids are required for a patient, and solutions are accordingly held in bottles of varying sizes and capacities. Normally, intravenous bottles are releasably retained within a gripping member such as a metal strap or the like which utilizes a toggle linkage member for gripping the fluid retaining bottle about the girth thereof. These bands are normally cinched about the bottle girth and are thereby relied upon for stable retention of the bottle within the retainer.

Frequently, intravenous bottles may have wet and slippery surfaces which cause the bottles to be difficult to handle and difficult to retain in upright disposition on the retainer means. Also, since fluids suitable for intravenous dispensing are received in bottles of varying sizes, frequent difficulty is encountered in providing adequate support for the individual intravenous feeding bottles during use.

SUMMARY OF THE INVENTION

In accordance with the present invention, an improved intravenous bottle retaining device is provided which utilizes an elongated split rubber sleeve member which is open-ended and generally radially flexible. Projection means are provided adjacent the bottom of the split sleeve member for releasably supporting an intravenous bottle within the sleeve and above the projection means, the bottle normally contacting the projection means at a point adjacent the shoulder thereof. In addition, strap means are secured to opposed free edges of the split sleeve member for releasably drawing the opposed free edges arcuately toward each other, thereby providing additional support for the bottle retained within the split rubber sleeve member. In addition, a support bracket means is provided which is slotted so as to receive an intravenous post therewithin, and adjustable pole-gripping means are provided for retaining the support bracket on the pole at any desired elevation. The design of the intravenous bottle retaining means of the present invention permits multiple bottles to be received and retained on a single pole member, with each of the bottles being rigidly and firmly held within the split sleeve bottle receiver.

Therefore, it is a primary object of the present invention to provide an improved intravenous bottle retaining means which is adapted to firmly and releasably retain an intravenous bottle member therewithin.

It is a further object of the present invention to provide an improved intravenous bottle retaining means which comprises an open-ended generally radially flexible split rubber sleeve member adapted to encircle the girth or circumference of an intravenous bottle held therewithin.

It is yet a further object of the present invention to provide an improved intravenous bottle retaining means which is adapted to firmly and releasably support an intravenous bottle therewithin, with projection means secured adjacent the bottom end of an open-ended generally radially flexible split rubber sleeve member for supporting an intravenous bottle at the shoulders thereof and above such projection means.

Other and further objects of the present invention will become apparent to those skilled in the art upon a study of the following specification, appended claims, and accompanying drawing.

BRIEF DESCRIPTION OF THE DRAWING

FIG. 1 is an elevational view showing a pair of intravenous bottle retaining means fabricated in accordance with the present invention, and mounted in operative disposition upon a support pole;

FIG. 2 is a top plan view of an intravenous bottle retaining means received on a support pole, with FIG. 2 being shown on a slightly enlarged scale, and with the base of the support pole being removed;

FIG. 3 is a vertical sectional view taken along the line and in the direction of the arrows 3—3 of FIG. 2, and illustrating a fragmentary portion only of the support pole, and further illustrating, in phantom, the configuration of an intravenous bottle retained therewithin; and FIG. 4 is a horizontal sectional view taken along the line and in the direction of the arrows 4—4 of FIG. 3.

DESCRIPTION OF THE PREFERRED EMBODIMENT

In accordance with the preferred modification of the present invention, and with particular attention being directed to FIG. 1 of the drawing, the intravenous assembly generally designated 10 includes a pair of bottle retaining means 11 and 12 retaining intravenous bottles 14 and 15 respectively, and further being received in operative disposition on support pole 16. Support pole 16 is, in turn, received on support pedestal 17, which pedestal may, in frequent instances, be provided with casters for ease in transport.

In FIG. 2, an intravenous bottle retaining means is illustrated in greater detail, with the bottle 14 being shown as received within the bottle retaining member. Specifically, a support bracket means 19 is provided which has a thumb screw 20 with a shank portion 21 engaging the periphery of pole 16, as illustrated in FIGS. 2 and 3. The support bracket is provided, at its outer end, with a bottle receiver in the form of an elongated split rubber sleeve member 22. Split rubber sleeve member 22 is open-ended, and is generally radially flexible, and is accordingly arranged to envelope, encircle, or otherwise hold an intravenous bottle therewithin. As is indicated, strap means are provided at opposed free edges of split rubber sleeve 22, such as is illustrated at 23, with the strap means 23 having a plurality of hook means secured to the free end thereof, for releasable locking engagement with a plurality of loop means secured to the outer surface of the split rubber sleeve 22. These loop means and hook means are commercially available as Velcro attachment members, and may find utility in connection with the intravenous bottle retaining means of the present invention.

As is apparent in FIG. 3, screws 27 and 28 are utilized to firmly secure split rubber sleeve 22 to support bracket 19. In addition, and as is illustrated in FIGS. 3 and 4, a plurality of projection means 29—29 are provided adjacent the bottom of said split rubber sleeve for releasably supporting an intravenous bottle within the sleeve. These projection members make contact with the shoulder portion of an intravenous bottle as is illustrated in FIG. 3, and thereby support the bottle above the individual projection means. As is apparent in FIG. 4, these projection means include one each adjacent opposed edges of the split rubber sleeve, with one being generally arcuately midway therebetween. As is apparent in FIG. 3, each of the projection means 29—29 is provided with a protruding head, preferably generally hemispherical in configuration, for making contact with the shoulder portion of a bottle retained therewithin, with one such generally hemispherical head being shown at 30.

For a coventional structure having a full opening to accommodate bottles of approximately 4 13/16th inch diameter, an original tube having a 4 ½ inch I.D. is employed, the wall thickness of the tube being ¼ inch. In a length of tubing of, for example, 5 inches, an opening force of 30 pounds is required to expand the tubing to receive or accept a bottle having an outer diameter of 4 13/16th inches. It has been found, however, that the overall length of the tubing is not particularly relevant to the opening pressure or force, however for most purposes, a convenient length of split tubing is approximately 5 inches.

Also, it will be appreciated that bottles of alternate or other diameters may also be employed and retained within this structure. It has been found that the walls of the tubing compress, grip, or otherwise restrain free downward motion of the tubing while the individual projection means 29—29 further restrain free downward motion of the contained bottle. Furthermore, the gripping force available from the arcuately spaced projections 29—29 does not interfere with the frictional gripping force normally exerted by the tubing. This is due to the fact that only arcuately spaced segments or portions of the tubing are forced outwardly, with the balance remaining intact, thereby preserving a substantial quantity of frictional contact between the retained bottle and the inner diameter of the intravenous bottle retaining means.

In order to place an intravenous bottle within the bottle retaining means, the operator or technician merely inverts the bottle and slips it through the split rubber sleeve member until the shoulder portion comes to rest on the individual projection means 29—29. When filled bottles of substantial weight are being utilized, it is frequently desirable to cinch up the structure by utilization of the coupling strap 23. These straps are held within the opposed free edges of the split rubber sleeve by any suitable means, such as the slots as at 26. Such an arrangement makes it possible for the operator or technician to provide a firm gripping force about the circumference of the intravenous bottle, particularly as is illustrated in FIGS. 1 and 4. The bottle retaining means of the present invention make it possible for a plurality of such bottles to be retained on a single support pole, and inasmuch as the support bracket 19 is generally short, danger of tipping of the pole by virtue of the presence of the bottles thereon is reduced.

We claim:
1. Intravenous bottle retaining means comprising
   a. a support bracket means having pole gripping means at the inner end thereof and an intravenous bottle receiver at the outer end thereof;
   b. said intravenous bottle receiver comprising an open-ended generally radially flexible split sleeve consisting essentially of resilient rubber material and having means securing said split sleeve to the outer end of said support bracket means, three substantially equally arcuately spaced apart radially inwardly extending hemispherical projections of small diameter disposed adjacent the bottom edge of said split sleeve for engaging and releasably supporting an intravenous bottle in inverted upright disposition within said split sleeve and generally above said projections; and
   c. strap means arranged for releasable securing to opposed free edges of said split sleeve for releasably drawing said opposed free edges arcuately toward each other.

2. Intravenous bottle retaining means as defined in claim 1 being particularly characterized in that said strap means include a plurality of loop means secured to the outer surface of said split sleeve, and a plurality of hook means secured to the free end of said strap for engaging said loop means.

3. Intravenous bottle retaining means as defined in claim 1 being particularly characterized in that said projections include one each of said projections adjacent opposed edges of said split sleeve, and one projection disposed generally arcuately midway therebetween.

* * * * *